(12) United States Patent
Rivarossa et al.

(10) Patent No.: US 7,202,230 B2
(45) Date of Patent: *Apr. 10, 2007

(54) USE OF HYALURONIC ACID DERIVATIVES IN THE PREPARATION OF BIOMATERIALS WITH A PHYSICAL HAEMOSTATIC AND PLUGGING ACTIVITY

(75) Inventors: Alberto Rivarossa, Fossano (IT); Daniele Pressato, Montegrotto Terme (IT)

(73) Assignee: Fidia Advanced Biopolymers, S.R.L., Abano Terme (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/139,878

(22) Filed: May 7, 2002

(65) Prior Publication Data

US 2003/0060448 A1 Mar. 27, 2003

Related U.S. Application Data

(63) Continuation of application No. 09/493,943, filed on Jan. 28, 2000, now abandoned, which is a continuation-in-part of application No. PCT/EP98/04716, filed on Jul. 28, 1998.

(30) Foreign Application Priority Data

Jul. 28, 1997 (IT) .............................. PD97A0170

(51) Int. Cl.
*A61K 31/728* (2006.01)
*A61K 9/70* (2006.01)
*C08B 37/08* (2006.01)

(52) U.S. Cl. ............................ 514/54; 514/62; 514/56; 536/21; 536/54; 536/18.7; 536/55.1; 536/55.2; 424/78.06; 424/486; 424/489; 424/488

(58) Field of Classification Search ................... 514/54, 514/56, 62; 536/21, 54, 18.7, 55.1, 55.2; 424/78.06, 486, 489, 488

See application file for complete search history.

(56) References Cited

U.S. PATENT DOCUMENTS 4,851,521 A 7/1989 della Valle
4,965,353 A 10/1990 della Valle
5,202,431 A 4/1993 della Valle
5,520,916 A 5/1996 Dorigatti et al.
5,922,358 A * 7/1999 Doutremepuich et al. .. 424/553
6,162,797 A * 12/2000 Zoppetti et al. ............. 514/54
6,723,709 B1 * 4/2004 Pressato et al. ............. 514/54

FOREIGN PATENT DOCUMENTS

| EP | 265116 A2 | | 4/1988 |
| EP | 517565 A2 | | 12/1992 |
| EP | 251905 B1 | | 11/1994 |
| EP | 571415 B1 | | 7/1995 |
| EP | 518710 B1 | | 5/1996 |
| EP | 654046 B1 | | 1/1998 |
| WO | 94/03212 | | 2/1994 |
| WO | WO 95/25751 | * | 9/1995 |
| WO | WO 97/07833 | * | 3/1997 |
| WO | 98/08876 | | 3/1998 |

OTHER PUBLICATIONS

Riesenfeld, Johan, "Quantitative Analysis of N-Sulfated, N-Acetylated. . .", Analytical Biochemisty, vol. 188 (1990), pp. 383-389.
Robbins, Thomas, "Microvascular Anastomosis: Vascular Cuff Technique", Plastic and Reconstructive Surgery, Mar. 1991.
Hart, "The effectof absorbable gelatin sponge on experimental microvascular anastomoses", British Journal of Plastic Surgery, vol. 40 (1987), pp. 300-304.
Hung, "Comparative Study of artery cuff and fat wrap in microvascular anastomosis in the rat", British Journal of Plastic Surgery, vol. 41 (1988), pp. 278-283.
Shaklee, "Hydrazinolysis of heparin and other glycosaminoglycans", Boichem. J., vol. 217, (1984), pp. 187-197.
O'Brien, "Microvascular Reconstructive Surgery", Churchill Livingstone (1977), pp. 40-50. and 79-90.

* cited by examiner

*Primary Examiner*—Shaojia Anna Jiang
*Assistant Examiner*—Devesh Khare
(74) *Attorney, Agent, or Firm*—Birch, Stewart, Kolasch & Birch LLP

(57) ABSTRACT

The present invention describes the use of polysaccharide derivatives for the preparation of biocompatible and biodegradable biomaterials with absorbent properties for body fluids and physical hemostatic activity, to be used in both venous and arterial vascular anastomoses to create a physical hemostatic barrier and to prevent scar tissue formation and formation of post-surgical adherence of the vessels to the surrounding tissues.

32 Claims, No Drawings

USE OF HYALURONIC ACID DERIVATIVES IN THE PREPARATION OF BIOMATERIALS WITH A PHYSICAL HAEMOSTATIC AND PLUGGING ACTIVITY

This application is a continuation of U.S. application Ser. No. 09/493,943, filed on Jan. 28, 2000 now abandoned, which is a continuation-in-part of PCT international application No. PCT/EP98/04716, which has an international filing date of Jul. 28, 1998, which designated the United States, the entire contents of which are hereby incorporated by reference.

OBJECT OF THE INVENTION

The present invention describes the use of polysaccharide derivatives for the preparation of biocompatible and biodegradable biomaterials with absorbent properties for body fluids and physical haemostatic activity. These biomaterials can be used during anastomotic surgery to create a physical haemostatic barrier by surrounding the surgical joining and to prevent scar tissue formation or the formation of post-surgical adherence of the vessels with the surrounding tissues.

BACKGROUND OF THE INVENTION

Anastomosis generally means the surgical joining of an opening formed between vessels or organs. This includes venous and arterial anastomosis of blood vessels (both venous and arterial), bowel anastomosis (including joining of segments of the intestinal tract after partial or total colectomy), the surgical implantation of catheters, and with endoscopic surgical procedures.

Vascular anastomosis means the surgical joining by suture of two ends of a divided blood vessel following the removal of a length of vessel because of thrombosis or arteriosclerosis, or the joining of two separate vessels for revascularization purposes (bypass and free flaps).

When the blood is allowed to flow through the vessel again after suture, one problem which may arise is the seepage of blood from between the stitches, especially if antithrombotic agents have been used. phenomena which may in turn cause intravascular thrombosis by the release of thrombogenic material. In addition, haematomas favour infection.

The "Vascular Cuff Technique" in microsurgery for vascular anastomosis is used with the following objectives:

to strengthen the vascular anastomosis and prevent the vessel from twisting or kinking or becoming compressed (T. H. Robbins, "Microvascular anastomosis: vascular cuff technique", Plastic and Reconstructive Surgery, 87, 567–568);

to achieve a haemostatic effect (N. B. Hart, British Journal of Plastic Surgery, 1987, 40, 300–304);

to reduce the number of suture stitches necessary (L. K. Hung et al., "Comparative study of artery cuff and fat wrap in microvascular anastomosis in the rat", British Journal of Plastic Surgery, 41, 278–283); and to create a suitable environment around the anastomosis to prevent adhesion with the surrounding tissues (T. H. Robbins, "Microvascular anastomosis: vascular cuff technique", Plastic and Reconstructive Surgery, 87, 567–568).

Until now, surgeons have tried to solve the problem of bleeding by using biomaterials containing haemostatic agents (N. B. Hart, British Journal of Plastic Surgery, 1987, 40, 300–304). However, although these do reduce bleeding time, they also have two undesirable side effects:

poor patency of the anastomosis;

increased occurrence of perivascular fibrosis and adhesions.

Moreover, since veins are less patent than arteries, it is very dangerous to use strong haemostatic agents at a venous level because of the risk of intravascular thrombosis.

Many authors advise against the use of biomaterials because they impede the natural healing of the tissue involved in anastomosis. Instead, the use of autologous tissues consisting of a segment of blood vessel wrapped around the anastomosis is favored (Plastic and Reconstructive Surgery, Vol. 87, No. 3, March 1991, pages 567–568).

Although the use of biomaterials constituted by ester derivatives (EP0216453) and autocrosslinked hyaluronic acid derivatives (EP0341745) is already known in the prevention of post-surgical adhesions (WO97/07833), nobody has ever before observed that they possess a physical haemostatic activity that supersedes the need to use a haemostatic agent with biochemical activity on the coagulation factors which may cause intravascular thrombosis.

Another advantage of these biomaterials is their ability to prevent the vessels from adhering to the surrounding tissues and to create, surprisingly, a suitable environment to favour correct tissue regeneration, unlike other types of biomaterial used in this type of surgery.

DETAILED DESCRIPTION OF THE INVENTION

The present invention describes the use of biocompatible and biodegradable biomaterials based on derivatives of hyaluronic acid, gellan and alginic acid, preferably derivatives of hyaluronic acid, which, because of their unexpected physical haemostatic properties, can be used to advantage in anastomosis, preferably vascular. During anastomatic surgery these biomaterials can be applied to the surgical joining, surrounding it, to create a physical haemostatic barrier. In addition, these biomaterials prevent post-surgical adhesion of the vessels to the surrounding tissues, reducing the formation of scar tissue. The following polysaccharide hyaluronic acid derivatives are preferred:

hyaluronic acid esters wherein a part or all of the carboxy functions are esterified with alcohols of the aliphatic, aromatic, arylaliphatic, cycloaliphatic, heterocyclic series (EP 0216453);

hyaluronic acid esters wherein a part of the carboxy functions are esterified with alcohols of the aralaphatic series and a second portion of the carboxy groups are derivatized with long chain aliphatic groups (WO 98/08876)

autocrosslinked esters of hyaluronic acid wherein a part or all of the carboxy groups are esterified with the alcoholic functions of the same polysaccharide chain or of other chains (EP 0341745);

crosslinked hyaluronic acid compounds wherein a part or all of the carboxy groups are esterified with polyalcohols of the aliphatic, aromatic, arylaliphatic, cycloaliphatic, heterocyclic series, generating crosslinking by means of spacer chains (EP 0265116 B1);

hemiesters of succinic acid or heavy metal salts of the hemiester of succinic acid with hyaluronic acid or with partial or total esters of hyaluronic acid (WO 96/35720);

sulphated derivatives (WO 95/25751) or N-sulphated derivatives (PCT/EP98/01973, filed Apr. 3,1998);

amide derivatives of hyaluronic acid;

partial esters and autocrosslinked ester derivatives of gellan (EP 0 518 710, EP 0 654 046); and ester derivatives of alginate (EP 251 905).

The succinic acid hemiester with hyaluronic acid, or with a hyaluronic acid total or partial ester useful in the present invention is characterized by having the following repeating unit (I):

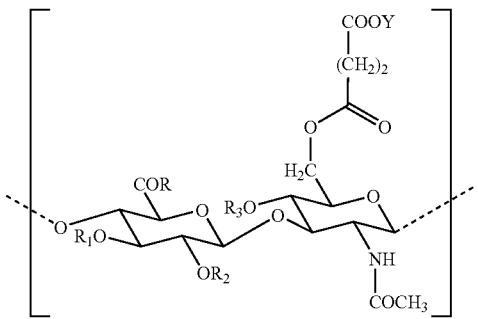

wherein $R_1$, $R_2$ and $R_3$, which are equal or different from each other, are H or $CO(CH_2)_2COOY$, wherein Y is a negative charge or H, and R is OH, $O^-$ or an alcoholic residue.

The heavy metal salt of the succinic acid hemiester with hyaluronic acid or with a hyaluronic acid total or partial ester are in particular characterized by having the following repeating unit (II):

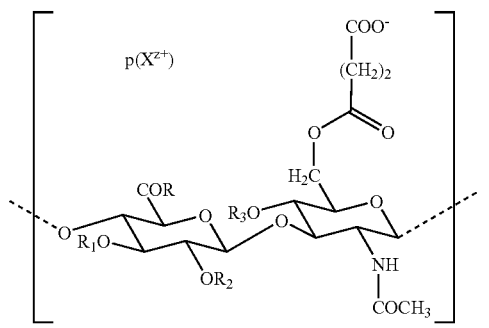

wherein $R_1$, $R_2$ and $R_3$, which are equal or different from each other, are H or $CO(CH_2)_2COO^-$, R is $O^-$, or an alcoholic residue, $(X^{z+})$ is a cation of a heavy metal in which z is a number comprised between 1 and 6, p is an integer or a decimal number, comprised between 0.1 and 5 provided that $p(X^{z+})$ is equal to the number of anionic groups $COO^-$ present in said repeating unit.

Hemiesters of succinic acid or heavy metal salts of the hemiester of succinic acid with hyaluronic acid or with partial or total esters of hyaluronic acid may be prepared according to the following steps:

a) converting the hyaluronic acid sodium salt into a salt selected from the group consisting of pyridinium, tetraalkylammonium, tetraarylammonium, tetraalkylphosphonium, tetraarylphosphonium salt, in the presence of water and an aprotic solvent, b) treating the solution coming from step (a) with succinic anhydride in the presence of an organic base, as the catalyst, removing the pyridinium, tetraalkylammonium, tetraarylammonium, tetraalkylphosphonium, or tetraarylphosphonium cation by dialysis, thereby obtaining the succinic acid hemiester having the repeating unit (I) provided that at least one of said repeating units (I) has R=OH or $O^-$, and optionally recovering the obtained product by freeze-drying.

c) treating the solution directly coming from the preceding step or an aqueous solution of the recovered solid product coming from the preceding step with an aqueous solution of an inorganic salt of the heavy metal, and recovering the product by filtration and vacuum drying.

In the case of the preparation of the heavy metal salt with the succinate hemiester of the total ester of hyaluronic acid, the following process may be used:

b') treating the hyaluronic acid ester dissolved or suspended in a mixture of water and an aprotic solvent with succinic anhydride in the presence of an organic base, as the catalyst, thereby obtaining the succinic acid hemiester having the repeating units (I) wherein R is a residue of an alcohol, and optionally recovering the obtained product by freeze-drying.

c') treating the solution directly coming from the preceding step or an aqueous solution of the recovered solid product coming from the preceding step with an aqueous solution of an inorganic salt of the heavy metal, and recovering the product by filtration and vacuum drying.

The term "heavy metal" encompasses any pharmaceutically active metal in the 4, 5 or 6 period of the periodic table.

The preferred heavy metal salts according to the present invention are those whose cation is: zinc, silver, copper, gold, cerium and tungsten salts of succinic derivatives of hyaluronic acid.

Hyaluronic acid or hyaluronic acid esters of any molecular weight can be used to prepare succinyl derivatives thereof. In the following examples, samples of hyaluronic acid with a molecular weight of between 30,000 and 760,000 Daltons were used, but this range is not critical.

Preferred succinic acid hemiesters of hyaluronic acid or hyaluronic acid esters are those having in the repeating unit (I) $R_1=R_2=R_3=H$ and the corresponding heavy metal salts wherein in the repeating unit (II) X is selected from the group consisting of: silver, gold, copper, and zinc, z is comprised between 1 and 3 and p is comprised between 0.3 and 2.

Another class of preferred succinic acid hemiesters with hyaluronic acid or hyaluronic acid esters are those having at least one repeating unit (I) wherein $R_1=R_3=H$ and $R_2=CO(CH_2)_2COOY$ and at least one repeating unit (I), wherein $R_2=R_3=H$, and $R_1=CO(CH_2)_2COOY$ has the above mentioned meanings and the corresponding heavy metal salts have at least one repeating unit (II) wherein $R_1=R_3=H$ and $R_2=CO(CH_2)_2COO^-$ and at least one repeating unit (II) wherein $R_2=R_{3\ 1=H.\ R1}=CO(CH_2)_2COO^-$, X is selected from the group consisting of: silver, gold, copper, and zinc, z is comprised between 1 and 3 and p is comprised between 0.6 and 3.

In step (a), above, the hyaluronic acid is preferably converted to the corresponding pyridinium salt. In particular this conversion encompasses a previous dissolution of the hyaluronic sodium salt in a mixture of water and dimethylformamide, a treatment with a cationic exchange resin for obtaining the corresponding free hyaluronic acid. After removal of the resin, the solution is neutralized with pyridine and the pyridinium salt is thus obtained.

In step (b) or (b') of both processes, the amount of succinic anhydride is not critical, although it is preferable to add high excess with respect to hyaluronic acid. In fact, the best results are obtained when the molar ratio of succinic anhydride/free OH groups present in the repeating unit (III)

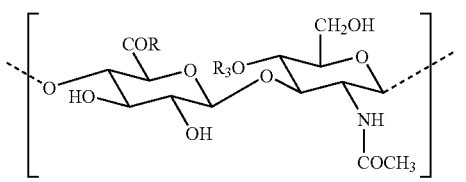
(III)

wherein R has the above-mentioned meanings, of the starting hyaluronic acid or hyaluronic acid partial ester, ranges between 15 and 90. Although the temperature is not critical, the best results are obtained if step (b) or (b') of both processes is carried out at 70° C. The preferred organic base used as catalyst in step (b) or (b') of both processes is selected from the group consisting of 4-dimethylaminopyridine, pyridine, or mixtures thereof. By using large amounts of 4-dimethylamminopyridine, a succinic acid hemiester with hyaluronic acid or a hyaluronic acid ester with a high degree of succinylation is obtained. By using pyridine alone or in a admixture with small quantities of 4-dimethylaminopyridine a succinic acid hemiester with hyaluronic acid with a low degree of succinylation is obtained. The stronger the reaction conditions, such as temperature, reaction times etc., the greater the degree of esterification of the derivatives formed.

For the preparation of the Ag salt of the succinate hemiester with hyaluronic acid or a hyaluronic acid ester, in step (c) or (c'), the succinic acid hemiester with hyaluronic acid or the succinic acid hemiester with hyaluronic acid ester is preferably treated with an aqueous solution of silver nitrate to form the silver salt of succinate hemiester with hyaluronic acid or hyaluronic acid ester. The Ag salt precipitates from the solution and is recovered by filtration or centrifugation. The precipitate is then washed with ethanol and vacuum dried at 40° C. The silver compounds of the succinyl derivatives are prepared in the complete dark. All the operations to prepare the silver nitrate solutions, and to prepare the succinyl silver hyaluronate were preformed in the dark and the resulting products were stored away from sources of light.

For the preparation of the Cu salts of the succinate hemiester with hyaluronic acid or a hyaluronic acid ester, in step (c) or (c') of both processes, the succinic acid hemiester with hyaluronic acid or the succinic acid hemiester with hyaluronic acid ester is preferably treated with an aqueous solution of $CuCl_2$ to form the Cu salt of succinate hemiester with hyaluronic acid or with the hyaluronic acid ester.

For the preparation of the Zn salts of the succinate hemiester with hyaluronic acid or a hyaluronic acid ester, in step (c) or (c') of both processes, the succinic acid hemiester with hyaluronic acid or the succinic acid hemiester with hyaluronic acid ester is preferably treated with an aqueous solution of $ZnCl_2$ to form the Zn salts of the succinate hemiester with hyaluronic acid or with the hyaluronic acid ester.

For the preparation of the Au salts of the succinate hemiester with hyaluronic acid or a hyaluronic acid ester, in step (c) or (c') of both processes, the succinic acid hemiester with hyaluronic acid or the succinic acid hemiester with hyaluronic acid ester is preferably treated with an aqueous solution of $HAuCl_4$ to form the Au salts of the succinate hemiester with hyaluronic acid or with the hyaluronic acid ester.

Specific examples of hemiester succinic acid derivatives of hyaluronic acid and hyaluronic acid esters include the following:

a) Example for the Preparation of Succinic Acid Hemiester with Hyaluronic Acid having the Repeating Unit (I)

EXAMPLE 1

A solution of sodium hyaluronate (HA-Na, 1 g, MW 160,000) in distilled water (35 ml) and N,N-dimethylformamide (DMF, 100 ml) was stirred for ten minutes in the presence of ion exchange resin (3 G. IR 120 H+), after which the resin was removed by filtration after further dilution with DMF (100 ml). The solution was then neutralized with an excess of pyridine (10 ml) to give the pyridine salt of hyaluronic acid (HA-Py). The viscous solution was then carefully evaporated in a vacuum to remove the water present, taking care not to allow the total volume of solution to drop below about 100 ml. This procedure was repeated three times, each time adding DMF (20 ml). The solution was then treated with succinic anhydride (3 g) and pyridine (10 ml) when being stirred at room temperature for 24 hours. The reaction mixture was then concentrated, gathered with distilled water (20 ml), dialyzed against distilled water (3 times, 750 ml) and freeze-dried to give hyaluronic acid succinylate (930 mg).

Table 1 shows the assignment of the chemical shift values of the $^{13}C$.n.m.r. (50.3 MHz) spectrum of sample 1.

TABLE 1

| Chemical Shift in δ ppm | Non-Modified HA | Modified HA | Other Groups |
|---|---|---|---|
| 101.49 | N-1 | | |
| 55.19 | N-2 | | |
| 83.30 | N-3 | | |
| 69.30 | N-4 | | |
| 76.23 | N-5 | | |
| 61.99 | N-6 | | |
| 103.82 | G-1 | | |
| 73.21 | G-2 | | |
| 79.98 | G-3 | | |
| 80.81 | G-4 | | |
| 76.23 | G-5 | | |
| 173.84 | G-6 | | |
| 175.63 | N=C=0 | | |
| 102.50 | | N-1 | |
| 83.00 | | N-3 | |
| 73.85 | | N-5 | |
| 64.08 | | N-6 | |
| 71.74 | | G-2 | |
| 29.79, 29.91 | | | $CH_2$ succinate |
| 175.35, 177.71 | | | C=0 succinate |

N.M.R. Analysis shows a degree of succinylation on carbon 6 of the N-acetylglucosamine (N-6) of 0.2 (mol of succinic acid/mol of repeating unit of the polymer).

EXAMPLE 2

A solution of sodium hyaluronate (HA-Na, 1 g, MW 30,000) in distilled water (35 ml) and N,N-dimethylformamide (DMF, 100 ml) was stirred in the presence of ion exchange resin (3 g, IR 120 H+) for 10 minutes and then the resin was removed by filtration after further dilution with DMF (100 ml). The solution was then neutralized with an excess of pyridine (10 ml) to give the pyridine salt of hyaluronic acid (HA-Py). The viscous solution was then carefully evaporated in a vacuum to remove the water present, without allowing the total volume of the solution to drop below about 100 ml. This water-removing procedure was repeated three times, each time with the addition of DMF (20 ml). The solution was then treated with succinic anhydride (3 g) and pyridine (10 ml) while being stirred at 70° C. for 24 hours. The reaction mixture was then concentrated, gathered with distilled water (20 ml), dialyzed against distilled water (3 times 750 ml) and freeze-dried to give hyaluronic acid succinylate (900 mg).

Table 2 reports the assignment of the chemical shift values of the $^{13}$C:n.m.r. spectrum (50.3 MHz) of sample 2).

TABLE 2

| Chemical shift in δ ppm | Non-Modified HA | Modified HA | Other Groups |
|---|---|---|---|
| 101.77 | N-1 | | |
| 54.33 | N-2 | | |
| 82.91 | N-3 | | |
| 69.93 | N-4 | | |
| 76.31 | N-5 | | |
| 60.95 | N-6 | | |
| 102.77 | G-1 | | |
| 72.58 | G-2 | | |
| 73.88 | G-3 | | |
| 80.94 | G-4 | | |
| 74.13 | G-5 | | |
| 170.00 | G-6 | | |
| 171.83 | N=C=0 | | |
| 102.50 | | N-1 | |
| 83.00 | | N-3 | |
| 73.85 | | N-5 | |
| 63.36 | | N-6 | |
| 70.73 | | G-2 | |
| 28.79 | | | $CH_2$ succinate |
| 168.98, 173.00 | | | C=O succinate |

N.M.R. analysis gives a degree of succinylation on carbon 6 of the Nacetylglucosamine (N-6) of about 0.45 (mol of succinic acid/mol of repeating unit.

EXAMPLE 3

A solution of sodium hyaluronate (HA-Na, 0.5 g, MW 160,000) in distilled water (35 ml) and N,N-dimethylformamide (DMF 100 ml) was stirred in the presence of ion exchange resin (3 G, IR 120 H+) for 10 minutes and then the resin was removed by filtration after further dilution with DMF (75 ml). The solution was then neutralized with an excess of pyridine (6 ml) to give the pyridine salt of hyaluronic acid (Ha-Py), the viscous solution was then carefully evaporated in a vacuum to remove the water present, without allowing the total volume of the solution to drop below about 50 ml. This water-removing procedure was repeated three times, each time with the addition of DMF (10 ml). The solution was then treated with succinic anhydride (2 g), 4-dimethylaminopyridine (10 mg) and pyridine (10 ml), while stirring at 70° C. for 48 hours. Further quantities of succinic anhydride were added (1 g) and pyridine (2.5 ml) and the mixture was stirred for another 24 hours. The reaction mixture was then concentrated, gathered with distilled water (20 ml), dialyzed against distilled water (3 times, 750 ml) for 3 days and freeze-dried to give hyaluronic acid succinylate (450 mg). The product was characterized by a high degree of viscosity when dissolved in water. The n.m.r. spectrum, in particular, was characterized by wide peaks, due to the sample's high degree of viscosity. The degree of modification was assessed by potentiometric assay, and proved to be 1.8 (mol of succinic acid/mol of repeating unit).

EXAMPLE 4

A solution of sodium hyaluronate (HA-Na, 0.5 G, MW 240,000) in distilled water (60 ml) and N,N-dimethylformamide (DMF 60 ml) was stirred in the presence of ion exchange resin (1 G. IR 120 H+) for 10 minutes, after which the resin was removed by filtration after further dilution with DMF (50 ml). The solution was then neutralized with an excess of pyridine (6 L) to give the pyridine salt of hyaluronic acid (HA-Py). The viscous solution was then carefully evaporated in a vacuum to remove the water present, without allowing the total volume of the solution to drop below about 100 ml. This water-removing procedure was repeated three times, each time with the addition of DMF (20 ml). The gelatin-like solution was then treated with succinic anhydride (2 g) and pyridine (5 ml) at 70° C., while being stirred for 18 hours. Further quantities of succinic anhydride (2.5 g) and 4-dimethylaminopyridine (200 mg) were added and the mixture was stirred for another 24 hours. The reaction mixture was then concentrated, gathered with distilled water (20 ml) and freeze-dried to give hyaluronic acid succinylate (450 mg). The product is characterized by being highly viscous when dissolved in water. The n.m.r. spectrum in particular is characterized by very wide peaks, due to the highly viscous character of the samples. The degree of modification was assessed by potentiometric assay and the result was 2.5 (mol of succinic acid/mol of repeating unit).

EXAMPLE 5

A solution of sodium hyaluronate (HA-Na, 1 g, MW 40,000) in distilled water (60 ml) and N,N-dimethylformamide (DMF 60 ml) was stirred in the presence of ion exchange resin (1 g, IR 120 H+) for 10 minutes, after which the resin was removed by filtration after further dilution with DMF (50 ML). The solution was then neutralized with an excess of pyridine (10 ml) to give the pyridine salt of hyaluronic acid (HA-Py). The viscous solution was then carefully evaporated in a vacuum to remove the water present, without allowing the total volume of the solution to drop below 50 ml. This water-removing procedure was repeated three times, each time with the addition of DMF (20 ml). The solution was then treated with succinic anhydride (3 g) and pyridine (10 ml) at 70° C. while stirring for 18 hours. Further quantities of succinic anhydride (2.5 g) and 4-dimethylaminopyridine (200 mg) were added and the mixture was stirred for another 24 hours. The reaction mixture, which was brown in color, was then concentrated, gathered with distilled water (20 ml), dialyzed against distilled water (3 times, 750 ml) and freeze-dried to give hyaluronic acid succinylate (850 mg). The degree of succinylation was assessed by potentiometric assay and was 3.5 (mol of succinic acid/mol of repeating unit).

EXAMPLE 6

A solution of sodium hyaluronate (HA-Na, 0.5 g, MW 760,000) in distilled water (60 ml) and N,N-dimethylformamide (DMF 60 ml) was stirred in the presence of ion exchange resin (1 g, IR 120 H+) for 10 minutes, after which the resin was removed by filtration after further dilution with DMF (50 ml). The solution was then neutralized with an excess of pyridine (6 ml) to give the pyridine salt of hyaluronic acid (HA-Py). The viscous solution was then carefully evaporated to remove the water present, without allowing the total volume of solution to drop below about 50 ml. This procedure was repeated three times, each time with the addition of DMF (20 ml). The gelatin-like solution was then treated with succinic anhydride (2 g) and 4-dimethylaminopyridine (200 mg) and the mixture was stirred for another 24 hours. The reaction mixture was then concentrated, gathered with distilled water (20 ml), dialyzed against distilled water (3 times, 750 ml) and freeze-dried to give hyaluronic acid succinylate (430 mg). The product is characterized by being highly viscous when dissolved in water. The n.m.r. spectrum in particular is characterized by very wide peaks, due to the highly viscous character of the samples. The degree of modification was assessed by potentiometric assay and was 2.5 (mol of succinic acid/mol of repeating unit).

b) Examples of the Preparation of Silver Salts of 0-succinyl Hyaluronate

EXAMPLE 7

100 mg of 0-succinyl hyaluronate, prepared as described in Example 1 were dissolved in 10 ml of distilled water. The polymer solution was then supplemented with 10 ml of a solution of $AgNO_3$ 1N. The white precipitate thus formed was kept in suspension while being stirred constantly for two hours, and was then gathered by filtration through a Buchner funnel, washed several times with ethanol and dried in a vacuum oven set at 40° C. All these operations were performed in the dark to avoid the formation of silver oxide. Atomic absorption analysis showed a silver content of 23.5% in weight, equal to 87% of the theoretical stoichiometric value.

EXAMPLE 8

70 mg of hyaluronic acid succinylate, prepared as described in Example 3 were dissolved in 14 ml of distilled water. The polymer solution, which was highly viscous, was supplemented with 14 ml of a solution of $AgNO_3$ 1N. A grey precipitate formed immediately and was kept in suspension while being constantly stirred for two hours, after which it was gathered by filtration through a Buchner funnel. It was washed several times with ethanol and dried in a vacuum oven set at 40° C. All these operations were performed in the dark to avoid the formation of silver oxide. Atomic absorption analysis showed the silver content to be 27% in weight, equal to 71% of the theoretical stoichiometric value.

EXAMPLE 9

100 mg of hyaluronic acid succinylate, prepared as described in Example 4, were dissolved in 20 ml of distilled water. The polymer solution, which was highly viscous, was supplemented with 20 ml of a solution of $AgNO_3$ 2N. A white precipitate formed immediately and was kept in suspension while being constantly stirred for two hours. It was then recovered by filtration through a Buchner funnel, washed several times with ethanol and dried in a vacuum oven set at 40° C. All these operations were performed in the dark to avoid the formation of silver oxide. Atomic absorption analysis showed the silver content to be 28.8% in weight, equal to 70.5% of the theoretical stoichiometric value.

EXAMPLE 10

100 mg of hyaluronic acid succinylate prepared as described in Example 5, were dissolved in 10 ml of distilled water. The polymer solution, which was high viscous, was supplemented with 10 ml of a solution of $AgNO_3$ 1N. A brownish precipitate formed immediately and was kept in suspension while being constantly stirred for two hours, after which it was recovered by filtration through a Buchner funnel, washed several times with ethanol and dried in a vacuum oven at 40° C. All these operations were performed in the dark to avoid the formation of silver oxide. Atomic absorption analysis showed the silver content to be 31%, equal to 70.2% of the theoretical stoichiometric value.

EXAMPLE 11

100 mg of hyaluronic acid succinylate, prepared as described in Example 6, were dissolved in 10 ml of distilled water. The polymer solution, which was highly viscous, was supplemented with 10 ml of a solution of $AgNO_3$ 1N. A brownish precipitate was immediately formed, which was kept in suspension while being constantly stirred for two hours, after which it was recovered by filtration through a Buchner funnel, washed several times with ethanol and dried in a vacuum oven set at 40° C. All these operations were performed in the dark to avoid the formation of silver oxide. Atomic absorption analysis showed the silver content to be 27% in weight, equal to 71% of the theoretical stoichiometric value.

c) Examples of the Preparation of Zinc Salts of Hyaluronic Acid Succinylate

EXAMPLE 12

100 mg of hyaluronic acid succinylate, prepared as described in Example 1 were dissolved in 10 ml of distilled water. The polymer solution was then supplemented with 10 ml of a solution of $ZnCl_2$ 0.2 N. The solution was stirred constantly for 2 hours, after which 3 volumes of ethanol were added to precipitate the soluble zinc salt. The precipitate was recovered by centrifugation at 3,000 rpm for 15 minutes, washed several times with ethanol and dried in a vacuum oven set at 40° C. Atomic absorption analysis showed a zinc content of 10%, equal to 101% of the theoretical stoichiometric value.

EXAMPLE 13

100 mg of hyaluronic acid succinylate prepared as described in Example 3 were dissolved in 20 ml of distilled water. The polymer solution, which was highly viscous, was supplemented with 20 ml of a solution of $ZnCl_2$ 2N. After the addition of zinc salt, a powdery precipitate was formed, which was recovered by centrifugation at 3,000 rpm for 15 minutes, washed several times with ethanol and dried in a vacuum oven set at 40° C. Atomic absorption analysis showed the zinc content in the sample to be 15.3%, equal to 105% of the theoretical stoichiometric value.

EXAMPLE 14

100 mg of hyaluronic acid succinylate prepared as described in Example 4 were dissolved in 20 ml of distilled water. The polymer solution, which was highly viscous, was supplemented with 20 ml of a solution of $ZnCl_2$ 2N. After the addition of zinc salt, a powdery precipitate was formed which was recovered by centrifugation at 3,000 rpm for 15 minutes, washed several times with ethanol and dried in a vacuum oven set at 40° C. Atomic absorption analysis showed the zinc content of the sample to be 17.7% in weight, equal to 105% of the theoretical stoichiometric value.

d) Example of the Preparation of the Copper Salt of Hyaluronic Acid Succinylate

EXAMPLE 15

100 mg of hyaluronic acid succinylate prepared as described in Example 5 were dissolved in 10 ml of distilled water. The polymer solution was then supplemented with 10 ml of a solution of $CuCl_2$ 2N. After the addition of copper salt, a blue precipitate was formed which was recovered by centrifugation at 3,000 rpm for 15 minutes, washed several times with ethanol and dried in a vacuum oven set at 40° C. Atomic absorption analysis showed the copper content of the sample to be 21.4% in weight, equal to 110% of the theoretical stoichiometric value. It is therefore probable that a small amount of copper salt is incorporated by the polymer during precipitation of the derivative.

e) Example of the Preparation of Gold Salt of Hyaluronic Acid Succinylate

EXAMPLE 16

100 mg of hyaluronic acid succinylate prepared as described in Example 3 were dissolved in 20 ml of distilled water. The polymer solution, which was highly viscous, was then supplemented with 20 ml of a solution of $HauCl_4$ 0.5N. After addition of gold salt, a precipitate was formed which was recovered by centrifugation at 3,000 rpm for 15 minutes, washed several times with ethanol and dried in a vacuum oven at 40° C. The gold content in the sample proved to be 13% in weight, equal to 44% of the theoretical stoichiometric value.

The sulfation of alcoholic hydroxyls present in the polymeric chain of hyaluronic acid or of a semisynthetic derivative of hyaluronic acid by the use of a suitable sulfating agent, can lead to the formation of new derivatives with chemical-physical characteristics, but most of all biological characteristics, which are different from those of the starting material.

Some particularly important semisynthetic derivatives of hyaluronic acid are esters thereof with alcohols of the aliphatic, araliphatic, heterocyclic and cycloaliphatic series, designated "HYAFF," that are described in U.S. Pat. Nos. 4,851,521, 4,965,353, and 5,202,431, and EP 0 216 453. In this case, the sulfation reaction no longer occurs in the homogeneous phase, but rather on the surface of the biomaterial in the heterogeneous phase, activating the exposed hydroxyl groups toward the reaction solvent.

The degree of sulfation that can be obtained directly on the biomaterial is an important characteristic, and requires careful kinetic control. To avoid the solubilization of the biomaterial, induced by the increased hydrophilic nature of the polymer which constitutes the matrix, the number of $-SO_3$ groups per dimeric unit must not exceed a certain level, generally less than 1.5–2, depending upon the degree of hydrophilicity of the starting biomaterial. For example, in the case of HYAFF 11 films, wherein all the carboxyls are involved in ester bonding with benzyl groups, the maximum degree of sulfation should not exceed 1.5.

The reagents commonly used for sulfation include the complex between sulfur trioxide and pyridine ($SO_3$-pyridine). The reaction is conducted by adding the sulfating reagent to a tetrabutylammonium salt of hyaluronic acid in solution, or to a solution of a hyaluronic acid ester, which, in the case of partial esters, contains the remaining carboxy functions in the form of tetrabutylammonium salts, in aprotic solvents such as dimethylsulfoxide, N,N'-dimethylformamide, and N-methylpyrrolidone in the temperature range of from about 0° C. to about 60° C.

Different degrees of sulfation, measured by the number of sulfate groups per disaccharide unit, are obtained by varying the quantity of $SO_3$-pyridine. The ratio between moles of hydroxyls and moles of sulfating reagent can vary between 1:1 and 1:12.

The present methods may be used to sulfate the polysaccharide chain of hyaluronic acid and its semisynthetic derivatives in a specific and homogeneous manner without causing loss of the polymer's characteristics, in particular its molecular weight.

By this method, it is possible to obtain new polymers with different levels of sulfation, but with the same molecular weight. Polymers with new biological characteristics can be obtained by using as starting materials biopolymers wherein the carboxy groups are salified with tetrabutylammonium salt. Such biopolymrs are not hemolytic.

A notable characteristic of these sulfated polysaccharides is their ability to increase blood coagulation time. For example, hyaluronic acid derivatives having a degree of sulfation greater than 2.5 exhibit good anticoagulant activity. In addition, the molecular weight of the starting polymer can also be significant in influencing the properties of the new sulfated biopolymers of the present invention.

In particular, at least four sulfated hyaluronic acid derivatives are notable due to their molecular weight and degree of sulfation. These are:

1. Hyaluronic acid having a molecular weight in the range between about 10,000 and about 50,000 Daltons, and having a degree of sulfation of 2.5, 3.0, or 3.5;

2. Hyaluronic acid having a molecular weight in the range between about 50,000 and about 250,000 Daltons, and having a degree of sulfation of 2.5, 3.0, or 3.5;

3. Hyaluronic acid having a molecular weight in the range between about 250,000 and about 750,000 Daltons, and having a degree of sulfation of 2.5, 3.0, or 3.5; and 4. Hyaluronic acid having a molecular weight in the range between about 750,000 and about 1,250,000 Daltons, and having a degree of sulfation of 2.5, 3.0, or 3.5.

The hyaluronic acid fractions having the molecular weights described above can be obtained by the use of membranes with particular molecular weight cut-off points, as is known in the art.

Among the semisynthetic ester derivatives of hyaluronic acid, polymeric matrices of HYAFF 11 (100% benzyl ester of hyaluronic acid) sulfated to degrees of 1.0 and 1.5, and HYAFF 11p75 (75% benzyl ester of hyaluronic acid) sulfated to degrees of 0.5 and 1.0, are particularly interesting.

Particular sulfated derivatives of hyaluronic acid may be prepared as follows.

a) Sulfation of Sodium Hyaluronate, Sulfation Degree 3

0.250 grams of the tetrabutylammonium salt of hyaluronic acid are solubilized in 10 ml of dimethylformamide (DMF). 1.305 grams of $SO_3$-pyridine solubilized in 10 ml of DMF are added to this solution under a flow of nitrogen. The solution is shaken for an hour at a temperature of between 4° C. and 0° C. About 200 ml of purified water, chilled to 0° C., are subsequently added. The pH of the mixture is brought to a value of between 8.5 and 9.5 by adding 1M sodium hydroxide. The derivative is then precipitated with 120 ml of ethyl alcohol. Sodium acetate is added to saturation, and the precipitate is left to deposit for between 1 and 24 hours at a temperature of between 0° C. and 4° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by nuclear magnetic resonance (NMR).

b) Sulfation of Sodium Hyaluronate, Sulfation Degree 3.5

0.250 grams of the tetrabutylammonium salt of hyaluronic acid are solubilized in 10 ml of dimethylformamide (DMF). 2.088 grams of $SO_3$-pyridine solubilized in 10 ml of DMF are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation, and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by nuclear magnetic resonance (NMR).

c) Sulfation of the Partial Ethyl Ester of Hyaluronic Acid: 75% of the Carboxy Groups are in the Form of the Ethyl Ester, Sulfation Degree 3

0.250 grams of the tetrabutylammonium salt of the 75% partial ethyl ester of hyaluronic acid (HYAFF-7p75) are solubilized in 10 ml of dimethylformamide (DMF). 1.305 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation, and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

d) Sulfation of the Partial Ethyl Ester of Hyaluronic Acid: 50% of the Carboxy Groups are in the Form of an Ethyl Ester, Sulfation Degree 2.5

0.250 grams of the tetrabutylammonium salt of the 50% partial ethyl ester of hyaluronic acid (HYAFF-7p50, 50% of the carboxy groups esterified with ethanol) are solubilized in 10 ml of dimethylformamide (DMF). 1.044 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

e) Sulfation of the Partial Ethyl Ester of Hyaluronic Acid: 25% of the Carboxy Groups are in the Form of an Ethyl Ester, Sulfation Degree 2

0.250 grams of the TBA salt of a partial ethyl ester of hyaluronic acid (HYAFF-7p25, 25% of the carboxy groups esterified with ethanol) are solubilized in 10 ml of dimethylformamide (DMF). 0.783 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation, and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

f) Sulfation of the Partial Benzyl Ester of Hyaluronic Acid: 75% of the Carboxy Groups are in the Form of a Benzyl Ester, Sulfation Degree 3.5

0.250 grams of the tetrabutylammonium salt of a partial ethyl ester of hyaluronic acid (HYAFF-11p75, 75% of the carboxy groups esterified with benzyl alcohol) are solubilized in 10 ml of dimethylformamide (DMF). 2.088 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation, and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

g) Sulfation of the Partial Benzyl Ester of Hyaluronic Acid: 50% of the Carboxy Groups are in the Form of a Benzyl Ester, Sulfation Degree 3

0.250 grams of the tetrabutylammonium salt of a partial ethyl ester of hyaluronic acid (HYAFF-11p50, 50% of the carboxy groups esterified with benzyl alcohol) are solubilized in 10 ml of dimethylformamide (DMF). 1.305 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

h) Sulfation of the Partial Benzyl Ester of Hyaluronic Acid: 25% of the Carboxy Groups are in the Form of a Benzyl Ester, Sulfation Degree 2

0.250 grams of the tetrabutylammonium salt of a partial ethyl ester of hyaluronic acid (HYAFF-11p25, 25% of the carboxy groups esterified with benzyl alcohol) are solubilized in 10 ml of dimethylformamide (DMF). 0.522 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation, and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

i) Preparation of Films of HYAFF 11, Sulfation Degree 1.5

0.250 grams of a film of HYAFF 11 are immersed in a bath of 250 ml of a mixture of chloroform:dimethyl-formamide in a ratio of 1:1. 50 ml of a solution obtained by solubilizing 3.4 grams of a complex of pyridine-$SO_3$ in dimethylformamide are then added.

The reaction is allowed to proceed for 2 hours at ambient temperature, after which the film is removed and then immersed in a bath of distilled water (100 ml), and lastly in a solution of water:ethanol, 50:50. The film is then oven-dried for 48 hours at 55° C.

j) Preparation of Films of HYAFF 11p75, Sulfation Degree 1

0.250 grams of a film of HYAFF 11p75 are immersed in a bath of 250 ml of a mixture of chloroform:dimethyl-formamide in a ratio of 1:1. 50 ml of a solution obtained by solubilizing 2.3 grams of a complex of pyridine-$SO_3$ in dimethylformamide are then added.

The reaction is allowed to proceed for 2 hours at ambient temperature, after which the film is removed and then immersed in a bath of distilled water (about 100 ml), and lastly in a solution of water:ethanol, 50:50. The film is oven-dried for 48 hours at 55° C.

N-sulfated derivatives of hyaluronic acids and derivatives thereof, optionally salified, with an anticoagulant or compound with antithrombotic activity, wherein the glucosamines are partially N-sulphated or partially N-sulphated and partially or totally O-sulphated in position 6, may be prepared as follows.

The following chemical process provides a method of using a well-characterized starting product, such as hyaluronic acid, for the selective sulphation of the amino group of glucosamine or the hydroxy group in the 6-position, to obtain new sulphated derivatives of hyaluronic acid with an unaltered range of molecular weights.

The term "partially 2-N-sulphated derivative" of hyaluronic acid means a product obtained by means of a controlled sulphation reaction of the amino group of the glucosamine of hyaluronic acid, previously N-deacetylated according to the procedure described by P. Shaklee (1984) Biochem. J. 217, 187–197. The reaction proceeds as illustrated below:

Diagram 1

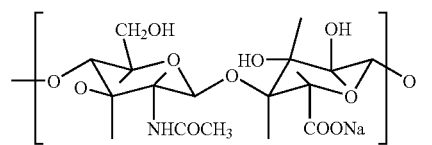

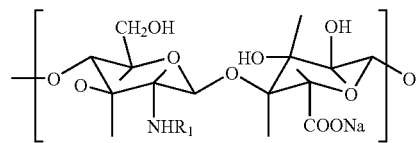

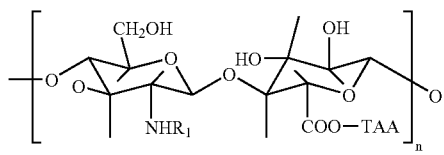

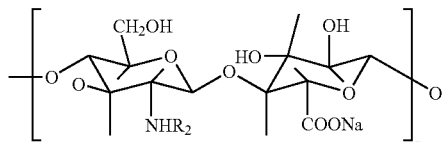

n: from 12 to 12500
$R_1$ = H, $COCH_3$
TAA = tetra-alkylammonium
$R_2$ = $SO_3$, $COCH_3$ The term "partially 2-N-sulphated and 6-O-sulphated derivatives" means the products of the chemical reaction illustrated in Diagram 1, wherein, besides the amino group of glucosamine, the primary hydroxy function of the same residue is also totally or partially involved in the sulphation reaction, as illustrated below:

Diagram 2

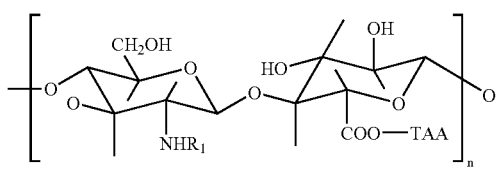

N-sulphation
6-O-sulphation

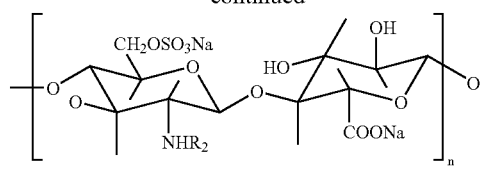

n: from 12 to 12500
R₁ = H, COCH₃
TAA= tetra-alkylammonium
R₂ = SO₃, COCH₃

The derivatives generated according to Diagrams 1 and 2 can be used as intermediate reactants in the preparation of compounds, according to the procedure described in European patent 0216453 B1, wherein the carboxy function of the glucuronic residue of hyaluronic acid, partially 2-N-sulphated or partially 2-N-sulphated and partially or totally 6-O-sulphated, is partially or completely reacted with alcohols of the aliphatic, aromatic, arylaliphatic, cycloaliphatic, heterocyclic series, producing the respective partial or total esters:

Diagram 3

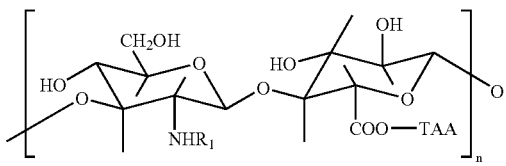

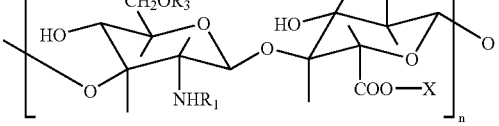

n: from 12 to 12500
R₁ = H, COCH₃
TAA= tetra-alkylammonium
R₂ = SO₃, COCH₃
R₃ = SO₃, H
X = alcoholic residue, Sodium Moreover, it is possible to use the synthetic derivatives according to Diagrams 1 and 2 as intermediates in the preparation of crosslinked compounds, according to the procedures described in European patents 0341745 B1 and 265116 B1 respectively, wherein a part or all of the carboxy groups belonging to the D-glucuronic residue are reacted: i) using condensing agents with the alcohol functions of the same polysaccharide chain or other chains, generating inner (or lactone) esters and intermolecular esters; ii) with poly-alcohols of the aliphatic, aromatic, arylaliphatic, cycloaliphatic, heterocyclic series, generating crosslinking by means of spacer chains.

The above-said sulphated compounds obtained according to the process of the present invention can be optionally salified with heavy metals, the heavy metals being selected from the group of metal elements in the 4th, 5th and 6th periods of the periodical table, such as silver, iron, cobalt, copper, zinc, arsenic, strontium, zirconium, antimonium, gold, cesium, tungsten, selenium, platinum, ruthenium, bismuth, tin, titanium, and mercury.

The sulphated derivatives can also be optionally salified with pharmacologically active substances such as antibiotics, antiinfective, antimicrobial, antiviral, cytostatic, antitumoral, antiinflammatory and wound healing agents, anesthetics, cholinergic or adrenergic agonists or antagonists, antithrombotic, anticoagulant, haemostatic, fibrinolytic and thrombolytic agents, proteins and their fragments, peptides, and polynucleotides.

The process for the preparation of the compounds of the present invention mainly consists of two steps, the first involving the controlled N-deacetylation of the natural polysaccharide, and the second involving the specific sulphation reaction of the primary hydroxy or free amino functions of glucosamine.

Fractions of hyaluronic acid from biological and fermentation sources, with a molecular weight of between 5,000 and 5,000,000 Da, preferably between 50,000 Da and 300,000 Da, are solubilized in hydrazine hydroxide with a purity of no less than 98%, in a concentration range of between 1 and 50 mg/ml, preferably between 5 and 25 mg/ml. This solution is then supplemented with hydrazine sulphate in a weight/volume concentration varying between 0.1 and 3%, preferably 1%.

The reaction is conducted within a temperature range of 40 to 90° C., preferably 60° C., under agitation, for as long as it takes to reach the desired degree of N-deacetylation.

Table 1 hereafter reports the yield expressed as the percentage of free amino groups, in terms of time expressed as hours of reaction:

TABLE 1

| Test | Temperature | Time (hours) | N-deacetylation (%)* |
|---|---|---|---|
| Dac 1** | 60° | 4 | 3 |
| Dac 2 | 60° | 8 | 5 |
| Dac 3 | 60° | 16 | 9 |
| Dac 4 | 60° | 24 | 14 |
| Dac 5 | 60° | 48 | 23 |
| Dac 6 | 60° | 72 | 36 |

*The percentage of N-deacetylation is determined according to the method of J. Riesenfeld (Analy. Bioch. 1990, vol. 188, pages 383–389).
**"DAc" = N-deacetylation The reaction is then stopped by precipitation with a polar solvent, preferably ethanol. The precipitate is partially vacuum-dried and treated with a solution of iodic acid with a molarity range of between 0.1 and 1M, preferably 0.5M, and lastly, with iodohydric acid at a concentration of 57% (w/v). The pH of the solution is maintained between 5 and 7 by adding a solution of sodium acetate (10% w/v).

The aqueous phase containing the modified polysaccharide is extracted by repeated treatments with diethylether and then, once the yellow color has completely disappeared, the solution is treated again with ethanol.

The precipitate which forms after further drying at 40° C., is solubilized in water at a concentration of between 10 ng/ml and 40 ng/ml, preferably 25 ng/ml, and the solution is percolated through a column containing an ion exchange resin activated with a tetraalkylammonium hydroxide, where the alkyl residue of the quaternary ammonium is constituted by a chain of between 1 and 4 carbon atoms. Tetrabutylammonium hydroxide is preferably used.

The percolated product, represented by the quaternary ammonium salt of the modified polysaccharide, is then freeze-dried.

Preparation of a Partially 2-N-sulphated Derivative:

Method A

The quaternary ammonium salt, preferably of tetrabutylammonium, of the partially N-deacetylated polysaccharide, is solubilized in an apolar solvent such as dimethyl sulphoxide, dimethyl formamide, dimethyl acetamide, N-methylpyrrolidone, preferably dimethyl formamide (DMFA), at a concentration of between 5 and 50 mg/ml (preferably 25 mg/ml).

The organic solution is supplemented with another solution obtained by solubilizing the sulphating complex constituted by dimethylformamide sulphotrioxide (DMFA-$SO_3$), in DMFA, at a concentration varying between 50 and 200 mg/ml and preferably 100 mg/ml. The quantity of complex to be used, expressed in moles of $SO_3$, proves surprisingly to be equivalent to the moles of amino groups released by the N-deacetylation reaction.

The sulphation reaction proceeds at a temperature of between 0° and 20° C., preferably 4° C. for no longer than 4 hours and is then stopped by adding cold, distilled water.

The reaction solvent is first purified by precipitating the partially 2-N-sulphated hyaluronic acid with ethanol and then dialysing the resolubilized product with distilled water.

Lastly, the solution is freeze-dried and the solid product thus obtained undergoes chemical-analytical characterization to determine the degree of N-sulphation and the mean molecular weight (Table 2).

TABLE 2

| Test | % deacetylation | % N-sulphation | mean MW (Da) |
|---|---|---|---|
| HA | 0 | 0 | 165,000 |
| HA-N-S1 | 5.0 (DAc 2) | 4.8 | 157,000 |
| HA-N-S2 | 14.2 (DAc 4) | 13.9 | 147,000 |
| HA-N-S3 | 23.5 (DAc 5) | 23.0 | 139,000 |
| HA-N-S4 | 36.1 (DAc 6) | 34.2 | 124,000 |

HA = hyaluronic acid
HA-N-S = N-sulphated hyaluronic acid

Preparation of a Partially 2-N-sulphated, 6-O-sulphated Derivative:

Method B

The quaternary ammonium salt, preferably of tetrabutylammonium, of the partially N-deacetylated polysaccharide is solubilized in an apolar solvent such as dimethylsulphoxide, demethylformamide, dimethylacetamide, N-methylpyrrolidone, preferably dimethylformamide (DMFA), at a concentration of between 5 and 50 mg/ml, preferably 30 mg/ml.

The organic solution is supplemented with another solution obtained by solubilizing the sulphating complex constituted by dimethylformamide sulphotrioxide (DMFA-$SO_3$), in DMFA, at concentrations varying between 50 and 200 mg/ml and preferably 100 mg/ml. The quantity of complex used, expressed as moles of $SO_3$, prove surprisingly to be equivalent to the moles of amino groups released by the N-deacetylation reaction.

The sulphation reaction proceeds at a temperature of between 0° and 20° C., preferably at 4° C. for 4 hours. A solution prepared by solubilizing the pyridine-sulphotrioxide complex in dimethylsulphoxide in such a quantity that the ratio between the moles of $SO_3$ of the sulphating agent and the moles of —$CH_2OH$ comes between 1.1 and 1.3. Larger quantities of reagent may favor any substitution reactions in other alcohol groups (secondary) of the polysaccharide chain.

The reaction then proceeds for another 16 hours at least after which it is stopped by adding cold, distilled water.

All subsequent steps concerning the purification of the modified polysaccharide are those described in "method A".

The analytical characterization performed on the derivatives obtained confirmed that the sulphation method proves surprisingly not only to substitute all the amino groups obtained by the partial N-deacetylation, but also results in the complete substitution of the primary alcohol group of the glucosamine residue of hyaluronic acid (Table 3).

TABLE 3

| Test | % N-deacetylation | % N-sulphation | % 6-O-sulphation |
|---|---|---|---|
| HA-N-O-S1 | 5.0 (DAc 2) | 4.8 | 100 |
| HA-N-O-S1 | 14.2 (DAc 4) | 13.9 | 99.2 |
| HA-N-O-S1 | 23.5 (DAc 5) | 23.0 | 98.9 |
| HA-N-O-S1 | 36.1 (DAc 6) | 34.2 | 96.5 |

HA-N-O-S1 = hyaluronic acid, N-sulphated and totally O-sulphated in position 6

Moreover, by varying the molar quantities of the pyridine-$SO_3$ complex according to the primary hydroxyl groups (molar ratio of between 0.1 and 1), "method B" enables a series of partially 2-N-sulphated and partially 6-O-sulphated derivatives to be obtained.

Specific examples of N-sulfated hyaluronic acid derivatives may be prepared as follows.

a) Preparation of Partially 2-N-sulphated Hyaluronic Acid (wherein about 5% of the N-acetyl Groups are Substituted by Sulphated Groups)

1.00 gr of HA from rooster combs, with a mean molecular weight of 181,000 Da, is solubilized in 50 ml of hydrazine monohydrate together with 0.5 gr of hydrazine sulphate.

The solution is maintained under agitation while the reaction is continued for 8 hours at 60° C., after which it is stopped by the addition of 100 ml of ethanol. The gelatinous precipitate thus formed is washed with ethanol and then dried at room temperature under reduced pressure.

The intermediate product is solubilized in a mixture constituted by 50 ml of water and 20 ml of a 10% solution of sodium acetate, and is treated lastly with 25 ml of a solution of iodic acid at a concentration of 0.5M. After about 30 minutes' reaction under agitation, the excess iodine is titrated with 5 ml of a 57% solution of iodohydric acid. During this operation it is preferable to keep the reaction container cold with ice. The rich brown solution is then treated at least five times with 30 ml aliquots of diethyl ether to extract the reaction residues from the aqueous solution containing the modified polymer. It is finally concentrated, at reduced pressure and at a temperature of 40° C., to a volume of about 40 ml and then percolated through a column filled with 20 ml of ion exchange sulphonic resin activated with a 40% solution w/v of tetrabutylammonium hydroxide.

The aqueous solution containing the modified polysaccharide in the form of tetrabutylammonium salt (HATBA) is then harvested and subjected to one lyophilization cycle.

1.30 gr of freeze-dried HA salt of TBA is solubilized in 45 ml of dimethylformamide and the solution thus obtained is supplemented with 0.6 ml of a solution of a complex of N-N dimethylformamide sulphotrioxide at a concentration of 50 mg/ml. The reaction continues for 5 hours at 4° C. under continuous, gentle agitation, after which it is stopped by adding 45 ml of cold, distilled water. Having neutralized the solution with NaOH 2 M, bringing it to a pH of between 7.5 and 8, it is then filtered through a Gooch filter with pore size G2 and treated with 250 ml of ethanol.

The precipitate thus formed is washed with at least 150 ml of ethanol and vacuum-dried for at least 16 hours, after which it is resolubilized in 50 ml of distilled water and then dialysed against 50 volumes of water.

The product is freeze-dried and then characterized to determine the percentage of N-substituted amino groups and its mean molecular weight.

| Weight of the freeze-dried product: | 0.72 gr; |
|---|---|
| yield: | 85% |
| moles of SO$_3$-/moles of HA (monomeric units) | 0.045 |
| moles of free —NH$_2$ groups/moles of HA: | 0.052 |
| % of de-N-acetylation: | 5.2% |
| % of re-N-sulphation | 4.5% |
| yield from the N-sulphation reaction: | 87% |
| mean molecular weight: | 174,000 Da | b) Preparation of Partially 2-N-sulphated Hyaluronic Acid (wherein about 25% of the N-acetyl Groups are Substituted with Sulphated Groups 1.2 gr of HA from rooster combs, with a mean molecular weight of 181,000 Da, is solubilized in 60 ml of hydrazine monohydrate together with 0.6 gr of hydrazine sulphate.

The solution is maintained under agitation while the reaction proceeds for 24 hours at 60° C., after which it is stopped by the addition of 120 ml of ethanol. The gelatinous precipitate thus formed is washed with ethanol and then dried at room temperature under reduced pressure.

The intermediate product is solubilized in a mixture constituted by 60 ml of water and 25 ml of a 10% solution of sodium acetate, and is treated lastly with 30 ml of a solution of iodic acid at a concentration of 0.5M. After about 30 minutes' reaction under continuous agitation, the excess iodine is titrated with 6 ml of a 57% solution of iodohydric acid. During this operation it is preferable to keep the reaction container cold with ice.

The rich brown solution is then treated at least five times with 40 ml aliquots of diethyl ether to extract the reaction residues from the aqueous solution containing the modified polymer. It is finally concentrated, at reduced pressure and at a temperature of 40° C., to a volume of about 50 ml and then percolated through an ion exchange column filled with 25 ml of sulphonic resin activated with a 40% solution w/v of tetrabutylammonium hydroxide.

The aqueous solution containing the modified polysaccharide in the form of tetrabutylammonium salt (HATBA) is then harvested and subjected to one lyophilization cycle.

1.65 gr of freeze-dried HA salt of TBA is solubilized in 55 ml of dimethylformamide and the solution thus obtained is supplemented with 3.0 ml of solution at a concentration of 50 mg/ml of a complex of N-N dimethylformamide sulphotrioxide. The reaction continues for 6 hours at 4° C. under continuous, gentle agitation, after which it is stopped by adding 55 ml of cold, distilled water. Having neutralized the solution with NaOH 2 M, bringing it to a pH of between 7.5 and 8, it is then filtered through a Gooch filter with pore size G2 and treated with 300 ml of ethanol.

The precipitate thus formed is washed with at least 150 ml of ethanol and vacuum-dried for at least 16 hours, after which it is resolubilized in 50 ml of distilled water and then dialysed against 50 volumes of water.

The product is freeze-dried and then characterized to determine the percentage of N-substituted amino groups and its mean molecular weight.

| Weight of the freeze-dried product: | 0.98 gr; |
|---|---|
| yield: | 89% |
| moles of SO$_3$-/moles of HA (monomeric units) | 0.23 |
| moles of free —NH$_2$ groups/moles of HA: | 0.24 |
| % of de-N-acetylation: | 24% |
| % of re-N-sulphation: | 23% |
| yield from the N-sulphation reaction: | 96% |
| mean molecular weight: | 161,000 Da | c) Preparation of Hyaluronic Acid, Partially 2-N-sulphated (wherein about 25% of the N-acetyl Groups are Substituted by Sulphated Groups) and 6-O-sulphated 5.0 gr of HA obtained by fermentation, with a mean molecular weight of 195,000 Da, is solubilized in 250 ml of hydrazine monohydrate together with 2.5 gr of hydrazine sulphate.

The reaction is maintained under agitation for 24 hours at 60° C., after which it is stopped by the addition of 500 ml of ethanol. The gelatinous precipitate thus formed is washed with ethanol and then dried at room temperature under reduced pressure.

The intermediate product is solubilized in a mixture constituted by 250 ml of water and 105 ml of a 10% solution of sodium acetate, and is treated lastly with 125 ml of a solution of iodic acid at a concentration of 0.5M. After about 30 minutes' reaction under continuous agitation, the excess iodine is titrated with 25 ml of a 57% solution of iodohydric acid. During this operation it is preferable to keep the reaction container cold with ice.

The rich brown solution is then treated at least five times with 150 ml aliquots of diethyl ether to extract the reaction residues from the aqueous solution containing the modified polymer. It is finally concentrated, at reduced pressure and at a temperature of 40° C., to a volume of about 200 ml and then percolated through a column filled with 100 ml of ion exchange sulphonic resin activated with a 40% solution w/v of tetrabutylammonium hydroxide.

The aqueous solution containing the modified polysaccharide in the form of tetrabutylammonium salt (HATBA) is then harvested and subjected to one lyophilization cycle.

6.0 gr of freeze-dried HA salt of TBA is solubilized in 300 ml of dimethylformamide and the solution thus obtained is supplemented with 13 ml of a solution of a complex of N-N dimethylformamide sulphotrioxide at a concentration of 50 mg/ml. The reaction continues for 6 hours at 4° C. under continuous, gentle agitation.

A second solution, constituted by 40 ml of a complex of pyridine sulphotrioxide solubilized in dimethyl sulphoxide at a concentration of 50 mg/ml is added to the reaction mixture.

Approximately sixteen hours later, 250 ml of cold, distilled water is added and, once the solution has been neutralized with NaOH 2 M to a pH of 8, it is then filtered through a Gooch filter with pore size G3 and treated with 1,250 ml of ethanol.

The precipitate thus formed is washed with at least 500 ml of ethanol and vacuum-dried for at least 16 hours, after which it is resolubilized in 250 ml of distilled water and then dialyzed against 50 volumes of water.

The product is freeze-dried and then characterized to determine the percentage of N-substituted amino groups, the degree of 6-O-sulphation and its mean molecular weight.

| | |
|---|---|
| Weight of the freeze-dried product: | 4.12 gr; |
| yield: | 82% |
| moles of $SO_3$-/moles of HA (monomeric units) | 1.24 |
| moles of free —$NH_2$ groups/moles of HA: | 0.26 |
| % of de-N-acetylation: | 26% |
| % of re-N-sulphation: | 24% |
| % of O-sulphation: | 100% |
| mean molecular weight: | 170,000 Da | d) Preparation of the Benzyl Ester of Hyaluronic Acid, Partially N-sulphated and O-sulphated 2.00 gr of the derivative obtained in Example 3 is solubilized in 100 ml of distilled water and the solution is percolated through a glass column previously filled with 40 ml of ion exchange resin activated with tetrabutylammonium hydroxide (TBA+ form). The eluate is freeze-dried and 3.3 gr of product is obtained.

The product is solubilized in a mixture constituted by 130 ml of N-methyl pyrrolidone and 1.3 ml of water, reacted at 4° C. with 0.29 ml of benzyl bromide. The reaction proceeds for 48 hours at 28° C., keeping the solution under agitation and away from sources of light, after which 300 ml of ethyl acetate is added.

The precipitate thus formed, mainly constituted by the modified polysaccharide, is washed with 100 ml of acetone and then vacuum-dried at room temperature, after which it is treated with 100 ml of a 10% solution w/v of sodium chloride.

At the end of the saline treatment (which lasts about one hour), the product is washed with 150 ml of water/acetone 20:80 and lastly with 100 ml of acetone.

After drying for 48 hours at 30° C., 0.92 gr at a yield of 80% is obtained.

| Characterization: | |
|---|---|
| % of esterification | 96% | e) Preparation of 10% Autocrosslinked Hyaluronic Acid, Partially N-sulphated and O-sulphated 2.00 gr of the derivative obtained in example 3 are solubilized in 100 ml of distilled water and the solution is percolated through a glass column filled with 40 ml of ion exchange resin activated with tetrabutylammonium hydroxide (TBA+ form). After freeze-drying the eluate, 3.3 gr of product are obtained.

The product is solubilized in a mixture formed by 165 ml of N-methyl pyrrolidone (NMP) and 0.8 ml of water, and then reacted with a solution obtained by solubilizing 205 mg of 2-chloro-1-methyl pyridine iodide in 8.2 ml of NMP. The reaction proceeds for 18 hours at −20° C., after which 165 ml of an aqueous solution of 3% ammonium acetate is added.

The mixture is constantly agitated for about 4 hours and then treated with 650 ml of ethanol. The precipitate thus formed is separated by filtration, washed with ethanol and then vacuum-dried for 24 hours.

The product is then treated with 60 ml of a 3% solution of sodium chloride so as to favor ion exchange and lastly reprecipitated by adding 180 ml of ethanol to the solution. After eliminating the supernatant the product is washed at least three times with 50 ml of ethanol and is then treated with 100 ml of acetone before being finally dried at 30° C. for 48 hours.

0.97 gr of sulphated and partially autocrosslinked derivative are thus obtained.

f) Preparation of a Film of Benzyl Ester of Hyaluronic Acid Partially N-sulphated and O-sulphated A solution of the benzyl ester of hyaluronic acid, partially N-sulphated and O-sulphated is prepared in dimethylsulphoxide at a concentration of 180 mg/ml.

A thin layer of solution is spread over a glass plate; the thickness of the layer of solution must be 10 times greater than that of the final film. The glass plate is immersed in ethanol which absorbs the dimethylsulphoxide without solubilizing the ester, which solidifies. The film is separated from the glass plate and repeatedly washed with ethanol, water and then again with ethanol.

The film obtained is dried under pressure for 48 hours at 30° C.

g) Preparation of the Silver Salt of the Partially 2-N-sulphated (25%) and 6-O-sulphated Hyaluronic Acid Derivative 0.50 gr of compound obtained according to example 2, is solubilized in 25 ml of distilled water and the solution obtained is percolated through a column filled with 16 cm$^3$ of strong ion exchange resin in H$^+$ form. The eluate is then harvested and freeze-dried. The intermediate product in acid form obtained by freeze-drying is treated with 20 ml of a 0.5 M solution of $AgNO_3$ for 60 minutes under agitation and away from the light.

Having eliminated the liquid phase by filtration, the product is thoroughly washed with 150 ml of distilled water and then with 50 ml of absolute ethanol. After vacuum-drying the sulphated hyaluronic acid derivative, silver salt, at 40° C., 0.649 gr are obtained (yield 95%).

Said hyaluronic acid derivatives can be used alone, in association with one another or with natural, semisynthetic or synthetic polymers. Some natural polymers that can be used are, for example, collagen, coprecipitates of collagen and glycosaminoglycans, cellulose, polysaccharides in the form of gels such as chitin, chitosan, pectin or pectic acid, agar, agarose, xanthan, gellan gum, alginic acid or the alginates, polymannan or polyglycans, starch, natural gums. The semisynthetic polymers, for example, can be selected from the group consisting of collagen crosslinked with agents such as aldehydes or precursors thereof, dicarboxylic acids or their halogenides, diamines, derivatives of cellulose, chitin or chitosan, gellan gum, xanthan, pectin or pectic acid, polyglycans, polymannan, agar, agarose, natural gum, glycosaminoglycans. Lastly, examples of synthetic polymers which can be used are as follows: polylactic acid, polyglycolic acid or copolymers of the same or their derivatives, polydioxanes, polyphosphazene, polysulphone resins, polyurethane resins, PTFE Of the hyaluronic acid esters to be used in the present patent application, it is preferable to use the benzyl esters, ethyl esters or propyl esters with 50–100% of the carboxy groups esterified, preferably 60–100%; more preferably 75–100% of the carboxy groups esterified. The benzyl ester with between 75% and 100% of its carboxy groups esterified and the remaining percentage salified with alkaline and alkaline earth metals, preferably with sodium, is particularly preferred. Also preferred are ester-derivatives of hyaluronic acid wherein a portion of the carboxy groups are esterified with an aralaphatic alcohol and a second portion of the carboxy groups are derivatized with straight aliphatic alcohols of 10–22 carbon atoms. Of such ester derivatives, the following compounds are particularly preferred:

hyaluronic acid esterified with benzyl alcohol (75%) and dodecyl alcohol (25%).

-hyaluronic acid esterified with benzyl alcohol (75% and hexadecyl alcohol (25%).

hyaluronic acid esterified with benzyl alcohol (75% and octadecyl alcohol (25%).

hyaluronic acid esterified with benzyl alcohol (75%) eicosanyl alcohol (20%) and salified with sodium (5%); and hyaluronic acid esterified with benzyl alcohol (75%), docosanyl alcohol (15%) and salified with sodium (10%)

The preferred crosslinked derivatives of the present invention are those with between 0.5% and 50% crosslinking; preferably between 0.5% and 20% and more preferably between 3% and 10%.

Said biomaterials can be prepared in the form of films, gels, sponges, gauzes, nonwoven fabrics, membranes, microspheres, microcapsules and guide channels according to the procedures reported in patents No. EP 0216453, EP 0341745, U.S. Pat. No. 5,520,916, EP 0517565, EP 0571415, WO 94/03212.

In one preferred embodiment of the invention, the polysaccharide derivatives are prepared in the form of threads. Of particular interest are threads made from the ester derivatives of hyaluronic acid, wherein a first part of the carboxy functions are esterified with an araliphatic alcohol such as benzyl alcohol, and second part of the carboxy functions are derivatized with long-chain, straight aliphatic alcohols and with between 10 to 22 carbon atoms, such as those disclosed in International Patent Application No. WO 98/08876.

The threads can optionally also contain other biocompatible polymers, such as polycaprolactone, polyglycolic acid, polylactic acid, PTFE and polyhydroxybutyrate. The threads made of the hyaluronic acid derivatives can be used as suture threads in anastomosis, particularly in the cardiovascular field, or the threads may be used to prepare mesh, knitted fabric, non-woven fabric, tubes or other materials to be used around the vessels or other organs which have undergone anastomosis.

Moreover, these biomaterials can be constituted by associations of derivatives of hyaluronic acid, gellan or alginate in various other forms and may contain pharmacologically active substances such as haemostatic and antiinflammatory agents, antibiotics, antithrombotics, factors able to activate plasminogens, and/or growth factors.

Of particular interest is the inclusion of haemostatic agents in the biomaterials. Examples of haemostatic agents which may be included are adrenalone, adrenochrome, aminochrome, batroxobin, carbazochrome salicylate, carbazochrome sodium sulfonate, cephalins, cotarnine, ethamsylate, factors VIII, IX, XIII, fibrinogen, 1,2-naphthoquinone, 1-naphthylamine-4-sulfonic acid, oxamarin, oxidized cellulose styptic collodion, sulmarin, thrombin, thromboplastin, tolonium chloride, tranexamic acid, vasopressin, and vitamins K2, K5, and K-S(II).

It may be of particular interest to use the biomaterials according to the present invention, alone or in association with one another, possibly with the above-said derivatives, in surgery such as cardiovascular and peritoneal surgery, employing their ability to absorb body fluids and thus reduce their accumulation in the sites involved in the surgical operation.

Said effect of absorbing the body fluids can be used to advantage in anastomotic surgery, wherein such accumulation is to be avoided.

Exemplified Embodiments of the Invention

EXAMPLE 1

Assessment of the response of vascular and perivascular tissue in rat to biomaterials comprising a benzyl ester of hyaluronic acid with 80% esterification in the form of a film and a 5% autocrosslinked derivative of hyaluronic acid in the form of a gel.

Materials and Methods

Preliminary analysis of 8 rats established that a preferable form of the biomaterial for post-anastomotic treatment of veins is a gel form, while in the case of post-anastomotic treatment of the arteries, a preferable treatment is a film, or a gel if bleeding is mild.

Gels are preferable with post-anastomotic treatment of veins because application of film to veins may cause excessive constriction of the vessel. Gels do not cause any such constriction, and the adherent properties of a gel allow it to seal the join and prevent bleeding through the stitches.

Because the blood pressure in arteries is very high, it is more suitable to use a film, or a gel may be appropriate in cases of only mild bleeding.

Forty-eight adult male Sprague Dawley rats with an average weight of 370 gr (between 295 gr and 480 gr) were used.

The rats were first anaesthetized with ether, after which they received 40 mg/kg of Pentothal by the intraperitoneal route and underwent dissection of the femoral vessels.

The diameters of the vessels were measured with graph paper before circulation was blocked with clamps and the vessel was cut.

The animals were subdivided into two groups of 24 rats.

1st Group—24 Rats

Each rat underwent venous anastomosis in both hindlimbs.

In this group, the veins of both hindlimbs first underwent anastomosis with between 8 and 10 suture stitches, after which one was treated with gel of the autocrosslinked compound spread around the suture line before the blood flow was restored, while the vein in the opposite limb was not treated with the biomaterial and therefore represented the control.

2nd Group—24 Rats

Each rat underwent venous anastomosis in one hindlimb and arterial anastomosis in the opposite hindlimb.

The veins were covered with gel of the autocrosslinked compound and the arteries with the film of hyaluronic acid benzyl ester.

Each group was subdivided into 4 subgroups of 6 rats each and their anastomosis were observed after 10, 15, 25 and 45 days respectively following application of the biomaterial, and the specimens were examined histologically.

Clinical assessment of the patency of the vessels was performed by the patency test according to O'Brien, B. McC. (1997, "Microvascular Reconstructive Surgery", Edinburgh: Churchill Livingstone).

Samples of perivascular tissue were observed to assess the occurrence of fibrosis and adhesions.

Results:

The results of the tests are summarized in Tables 1 and 2

Fifteen femoral veins proved to be occluded and 57 patent (patency rate 79.17%).

TABLE 1

| GROUPS Treatment | 1st | | 2nd | |
|---|---|---|---|---|
| | Control veins | Veins + gel | Veins + gel | Arteries + film |
| No. vessels | 24 | 24 | 24 | 24 |
| No. occluded vessels | 3 | 3 | 3 | 1 |
| No. occluded vessels with thrombosis | 5 | — | 1 | — |
| No. patent vessels | 16 | 21 | 20 | 23 |
| % patency | 66.6 | 87.5 | 83.3 | 95.83 | veins + gel    veins treated with autocrosslinked hyaluronic acid gel
arteries + film    arteries treated with film of hyaluronic acid benzyl ester

TABLE 2

| Treatment | veins + gel (1st + 2nd groups) | control veins | arteries + film |
|---|---|---|---|
| No vessels | 48 | 24 | 24 |
| patency | 41 (85.41%) | 16 (66.66%) | 23 (96%) |
| mean bleeding time (sec.) | 23 (0–59) | 54.3 (5–122) | 117 (80–178) |
| diameter of vessel | 1.54 mm | 1.49 mm | 0.93 mm |

The results showed a reduction in mean bleeding time, particularly in the case of the veins treated with gel made of the autocrosslinked compound, less fibrosis and reduced formation of scar tissue around the treated vessel.

Histological analysis of the specimens performed on about 20 vessels randomly chosen from the $1^{st}$ and $2^{nd}$ groups after different days showed that the veins and arteries were generally patent, albeit slightly narrowed in some cases by mild fibrous thickening of the intima. There was just one case of a small thrombus which could be seen adhering to the vessel wall.

The endothelium was not hypertrophic, it had no visible fibroses or adherence and appeared fine and even all over. Hematoxylin-eosin staining did not reveal any other structural alterations to the vascular walls besides sporadic areas of fibrosis attributable to the scarring effects of surgery.

The surgical material used for the operation, appearing under the microscope as an amorphous, foreign, birefringent material, was surrounded by patches of granulomatous reaction characterised by the presence of lymphocytes, plasma cells and multinucleate histocytes.

There were no signs of granulocyte-type inflammation.

The invention being thus described, it is clear that these methods can be modified in various ways. Such modifications are not to be considered as divergences from the spirit and purpose of the invention, and any modification which may appear evident to an expert in the field is to be considered as coming within the scope of the following claims:

The invention claimed is:

1. A method of creating a physical haemostatic barrier to effect haemostasis comprising applying to a surgical joining of two tissues during anastomotic surgery a biomaterial comprised of at least one hyaluronic acid or a derivative thereof to effect haemostasis by creating a physical haemostasic barrier.

2. A method of creating a physical haemostatic barrier to effect haemostasis comprising applying to a surgical joining of two tissues during anastomotic surgery a biomaterial comprised of at least one hyaluronic acid or a derivative thereof and at least one member of the group consisting of natural polymers, semisynthetic polymers, synthetic polymers and pharmacologically active substances to effect haemostasis by creating a physical haemostatic barrier.

3. The method according to claim 1, wherein said hyaluronic acid derivative is a hyaluronic acid ester wherein part or all of the carboxylic functions are esterified with an alcohol of the aliphatic, aromatic, arylaliphatic, cycloaliphatic or heterocyclic series.

4. The method according to claim 1, wherein said hyaluronic acid derivative is an autocrosslinked ester of hyaluronic acid wherein part or all of the carboxy groups are esterified with an alcoholic function of the same or other polysaccharide chain.

5. The method according to claim 1, wherein said hyaluronic acid derivative is a crosslinked compound of hyaluronic acid wherein part or all of the carboxy groups are esterified and crosslinked with a polyalcohol of the aliphatic, aromatic, arylaliphatic, cycloaliphatic or heterocyclic series.

6. The method according to claim 1, wherein said hyaluronic acid derivative is a hyaluronic acid ester derivative wherein a first portion of the carboxy groups is esterified with an araliphatic alcohol and a second portion of the carboxy groups is derivatized with straight aliphatic alcohols of 10–22 carbon atoms.

7. The method according to claim 1, wherein said hyaluronic acid derivative is a hemiester of succinic acid or a heavy metal salt of the hemiester of succinic acid with hyaluronic acid or with a partial or total ester of hyaluronic acid.

8. The method according to claim 1, wherein said hyaluronic acid derivative is sulphated or N-sulphated.

9. The method according to claim 2, wherein said natural polymers are selected from the group consisting of collagen, coprecipitates of collagen and glycosaminoglycans, cellulose and polysaccharides in the form of gels.

10. The method according to claim 2, wherein said semisynthetic polymers are selected from the group consisting of collagen crosslinked with aldehydes or precursors of the same, dicarboxylic acids or their halogenides, diamines, derivatives of cellulose, hyaluronic acid, chitin, chitosan, gellan gum, xanthan, pectin or pectic acid, polyglycans, polymannan, agar, agarose, natural gums and glycosaminoglycans.

11. The method according to claim 2, wherein said synthetic polymers are selected from the group consisting of polylactic acid, polyglycolic acid or copolymers of the same or the derivatives thereof, polydioxane, polyphosphazene, polysulphone resins, polyurethane resins and PTFE.

12. The method according to claim 2, wherein said pharmacologically active substance is a member selected from the group consisting of anti-inflammatory agents, haemostatic agents, antibiotics, antithombotics and growth factors.

13. The method according to claim 2, wherein said pharmacologically active substance is fibrinogen or thrombin.

14. The method according to claim 3, wherein said ester derivative of hyaluronic acid is esterified within a range of 60–100%.

15. The method according to claim 4, wherein said autocrosslinked derivative of hyaluronic acid is autocrosslinked within a range of 0.5–20%.

16. The method according to claim 1 or 2, wherein said biomaterials are in the form of films, gels, sponges, gauzes, nonwoven fabrics, membranes, microspheres, microcapsules, threads, guide channels and associations thereof.

17. The method according to claim 1 or 2, wherein said surgery further comprises cardiovascular and peritoneal surgery.

18. The method according to claims 1 or 2, wherein said biomaterial surrounds the anastomotic joining.

19. The method according to claim 18, wherein said anastomotic joining involves veins and said biomaterial is a gel.

20. The method according to claim 18, wherein said anastomotic surgery involves arteries and said biomaterial is a film.

21. The method according to claim 1 or 2, wherein said surgical joining involves veins and said biomaterial is a gel.

22. The method according to claim 15, wherein said autocrosslinked derivative is autocrosslinked within a range of 3–10%.

23. A method of creating a physical haemostatic barrier to effect haemostasis comprising applying to a surgical joining of two tissues during anastomotic surgery a biomaterial comprised of at least one hyaluronic acid or a derivative thereof selected from the group consisting of esters, partial esters, autocrosslinked esters, crosslinked via spacer chains, hemiesters, sulphated, N-sulphated and amides to effect haemostasis by creating a physical haemostatic barrier.

24. A method of creating a physical haemostatic barrier to effect haemostasis comprising applying to a surgical joining of two tissues during anastomotic surgery a biomaterial comprised of at least one hyaluronic acid or a derivative thereof selected from the group consisting of esters, partial esters, autocrosslinked esters, crosslinked via spacer chains, hemiesters, sulphated, N-sulphated and amides, and at least one member of the group consisting of natural polymers, semisynthetic polymers, synthetic polymers and pharmacologically active substances to effect haemostasis by creating a physical haemostatic barrier.

25. A method of creating a physical haemostatic barrier to effect haemostasis comprising applying to a surgical joining of two tissues during anastomotic surgery a biomaterial comprised of at least one hyaluronic acid derivative selected from the group consisting of esters, partial esters, autocrosslinked esters, crosslinked via spacer chains, hemiesters, sulphated, N-sulphated and amides to effect haemostasis by creating a physical haemostatic barrier.

26. A method of creating a physical haemostatic barrier to effect haemostasis comprising applying to a surgical joining of two tissues during anastomotic surgery a biomaterial comprised of at least one hyaluronic acid derivative selected from the group consisting of esters, partial esters, autocrosslinked esters, crosslinked via spacer chains, hemiesters, sulphated, N-sulphated and amides, and at least one member of the group consisting of natural polymers, semisynthetic polymers, synthetic polymers and pharmacologically active substances to effect haemostasis by creating a physical haemostatic barrier.

27. The method according to claim 1 or 2, wherein said derivative is an ester or hemiester.

28. The method according to claim 27, wherein said hemiester is a hemiester of succinic acid.

29. The method according to claim 1 or 2, wherein said derivative is an amide.

30. The method according to claim 1 or 2, wherein said derivative is sulphated or N-sulphated.

31. The method according to claim 1 or 2, wherein said derivative is crosslinked or autocrosslinked.

32. The method according to claim 30, wherein said crosslinked derivative results from crosslinking by means of spacer chains.

* * * * *